(12) United States Patent
Florent et al.

(10) Patent No.: US 12,232,825 B2
(45) Date of Patent: Feb. 25, 2025

(54) SYSTEM FOR IMAGE PROCESSING (71) Applicant: KONINKLIJKE PHILIPS N.V., Eindhoven (NL)

(72) Inventors: Raoul Florent, Ville d'Avray (FR); Claire Levrier, Rueil-Malmaison (FR); Bart Pierre Antoine Jozef Hoornaert, Arendonk (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 315 days.

(21) Appl. No.: 17/770,324

(22) PCT Filed: Oct. 20, 2020

(86) PCT No.: PCT/EP2020/079424
§ 371 (c)(1),
(2) Date: Apr. 20, 2022

(87) PCT Pub. No.: WO2021/078701
PCT Pub. Date: Apr. 29, 2021

(65) Prior Publication Data
US 2022/0378515 A1    Dec. 1, 2022

(30) Foreign Application Priority Data
Oct. 21, 2019   (EP) ..................... 19290107

(51) Int. Cl.
*A61B 34/00*   (2016.01)
*A61B 6/00*    (2006.01)
*A61B 6/12*    (2006.01)
*A61B 6/46*    (2024.01)
*A61B 34/20*   (2016.01)

(52) U.S. Cl.
CPC ............... *A61B 34/20* (2016.02); *A61B 6/12* (2013.01); *A61B 6/4441* (2013.01); *A61B 6/463* (2013.01); *A61B 6/487* (2013.01); *A61B 6/5211* (2013.01); *A61B 6/547* (2013.01)

(58) Field of Classification Search
CPC ...................................... A61B 34/20
See application file for complete search history.

(56) References Cited

U.S. PATENT DOCUMENTS

| 8,764,291 B2 | 7/2014 | Ruijters |
| 2011/0110572 A1 | 5/2011 | Guehring |
| 2015/0305703 A1 | 10/2015 | Kim |
| 2017/0135654 A1 | 5/2017 | Van Daal |
| 2017/0290559 A1 | 10/2017 | Gemmel |

FOREIGN PATENT DOCUMENTS

WO    2016141449 A1    9/2016

OTHER PUBLICATIONS

International Search Report and Written Opinion of PCT/EP2020/079424, dated Jan. 13, 2021.
(Continued)

*Primary Examiner* — Joseph M Santos Rodriguez (57) ABSTRACT

The invention is directed to a system (100) for image processing, which is capable of improving an usability of an imaging device during an intervention.

13 Claims, 2 Drawing Sheets

(56) References Cited

OTHER PUBLICATIONS

Patil, Meru A. et al A Machine Learning Framework for Auto Classification of Imaging System exams in Hospital Setting for Utilization Optimization, Conf. Proceedings; Annual International Conf. of the IEEE Engineering in Medicine and Biology Society, vol. 2016, pp. 2423-2426, Aug. 2016.

Bredno, J. et al "Algorithmic Solutions for Live Device-to-Vessel Match", Proceedings of SPIE, vol. 5370 Medical Imaging 2004, pp. 1486-1497.

Patil, Ravindra B. et al "Predictive Modeling for Corrective Maintenance of Imaging Devices from Machine Logs", IEEE 2017, pp. 1676-1679.

Schaller, Christian et al "Inverse C-arm Positioning for Interventional Procedures using Real-Time Body Part Detection", Medical Image Computing and Computer-Assisted Intervention, Miccai, vol. 12, pp. 549-556, 2009.

Bangalore, Sripal et al "Right Heart Catheterization, Coronary Angiography, and Percutaneous Coronary Intervention", Circulation, 2011, pp. e428-e433.

Siemens Healthcare GmbH, Frederick Jeske-Schoenhoven, Reference No. PR2017110086HCEN, 2017.

SYSTEM FOR IMAGE PROCESSING

CROSS-REFERENCE TO PRIOR APPLICATIONS

This application is the U.S. National Phase application under 35 U.S.C. § 371 of International Application No. PCT/EP2020/079424, filed on Oct. 20, 2020, which claims the benefit of European Patent Application No. 19290107.2, filed on Oct. 21, 2019. These applications are hereby incorporated by reference herein.

FIELD OF THE INVENTION

The invention is directed to a system for image processing, a computer-implemented method for image processing, a computer program and an imaging device.

BACKGROUND OF THE INVENTION

In general, the medical imaging systems are used for Percutaneous Coronary Intervention (PCI) in catheter laboratories, to treat cardiac stenosis. Typically, a catheter is inserted into the vascular system at an access site, it is advanced along large vessels to the vascular structure that requires treatment. Contrast agent is injected via the catheter and cathlab x-ray equipment records an angiographic sequence that shows the vessels when filled with contrast agent. In general, diagnosis and intervention planning are based on such diagnostic angiograms. During intervention, a flexible, partially or fully radio-opaque guidewire is advanced to the affected vascular structures (e.g. stenosis in coronaries, neurovascular aneurysms, or arterio-venous malformations). Fluoroscopic low-dose x-ray surveillance visualizes the guidewire and allows for the hand-eye coordination of the interventionalist while advancing the guidewire. When positioned, the guidewire serves as a rail to deliver interventional devices (e.g. balloons for dilation and stent delivery, detachable coils for aneurysm clotting).

In the field of radiology, automatically positioning of a diagnostic imaging system is a complex subject, since not only the position of the patient has to be assessed but in addition the image quality of the medical image data has to be sufficient. In addition, medical imaging during an intervention is usually carried out manually since it is a very complex procedure. Usually, a plurality of guidelines for positioning the medical imaging device are provided for assisting medical personnel.

SUMMARY OF THE INVENTION

With embodiments of the invention, an improved system for image processing is provided.

The invention is defined by the independent claims. Further embodiments and advantages of the present invention are incorporated in the dependent claims and the description.

Technical terms are used by common sense. If a specific meaning is conveyed to certain terms, definition of terms will be given in the following in the context which the terms are used.

According to a first aspect of the invention, a system for imaging processing comprises an identification unit and a compliance unit. The identification unit is configured for receiving an intervention focus. For instance, the received intervention focus may be indicative (or reflects, or specifies) of which intervention is depicted (or pictured, or shown, or represented, or outlined, or sketched) in an image data and reflects which anatomical region is undergoing the intervention de in the image data. The identification unit is configured for determining an orientation parameter indicative for an orientation of an imaging device, when generating the image data. The compliance unit comprises and/or is configured for receiving a predefined threshold for the orientation parameter specific for the received intervention focus. Furthermore, the compliance unit is configured for comparing the determined orientation parameter and the predefined threshold. In addition, the compliance unit is configured for calculating an optimized orientation parameter for the orientation of the imaging device based on the comparison. Furthermore, the compliance unit is configured for generating a signal indicative for the orientation of the imaging device based on the calculated optimized orientation parameter.

The advantage of this embodiment is that the positioning of a imaging device can be improved during intervention. By providing a solution for such a dynamic process, the usability of an imaging device during an intervention can be improved. In an embodiment, predefined guidelines are used in order to increase the usability of the imaging device during an intervention since the system is capable of comparing the current situation of the intervention with the predefined guidelines.

In other words, the system for image processing is configured for the processing of medical image data. The system can comprise or can have an identification unit and/or an identification logic. Furthermore, the system can comprise and/or can have a compliance unit and/or a compliance logic. Furthermore, the identification unit can be configured for receiving, downloading and/or accessing image data representing an intervention. From the image data, the intervention focus is identified automatically, for example using an artificial intelligence (AI) algorithm.

Within the present context, the "intervention focus", or focus of the intervention, is understood as a location in an image at which a doctor or physician would focus during (a step of) the intervention. In clinical practice, it is common to observe the clinician intensely focusing on a local region of an image. Advantageously, the intervention focus is herein automatically determined from a clinical context derived from image data, in particular involving the identification of one or more interventional devices and an anatomical region in an image representing the intervention, or a sequence of such images.

Furthermore, the identification unit is configured for determining an orientation parameter indicative for an orientation of an imaging device, in particular the orientation of the image device at the time that the image data used for determining the intervention focus was acquired.

For example, the orientation parameter is determined by means of recording a current position of the imaging device, in particular the geometry including zoom, angulation table positioning and the like, when it is determined that the current image data represents the intervention focus.

For example, the orientation parameter represents a rotation and/or an angulation of a C-arm X-ray system, during a generation respectively acquisition of the image data.

Furthermore, the compliance unit can receive a guideline corresponding to a type of intervention. In particular, such guideline may include a system positioning guideline for example for a Percutanous Coronary Intervention (PCI) procedure.

In an embodiment, based on such guideline, a guideline position parameter corresponding to the intervention focus is determined. For example, starting from a PCI system positioning guideline, a preferred angulation and/or orientation for a C-arm X-ray system may be determined.

Subsequently, the guideline position parameter and the received actual orientation parameter may be compared and a deviation between the two may be calculated. In an embodiment, if the calculated deviation exceeds a predefined threshold, a further action may be triggered, such as generating a signal indicative of a positioning discrepancy for example.

For example, the predefined threshold respectively a pre-specified boundary value for the orientation parameter may be specific for and/or in dependency of the received intervention focus and in particular the corresponding guideline position parameter. Furthermore, the predefined threshold may comprise a set of several different specified boundaries, in particular specified boundaries based on the intervention focus such as a set of corresponding guideline position parameters.

In certain examples, the guideline and/or the set of guidelines can be accessed by the compliance unit via a computer network structure, e.g. Cloud, or any other online and/or network storage.

In an embodiment, the compliance unit is configured for calculating respectively generating an orientation parameter, in particular an optimized, improved and/or enhanced orientation parameter for amending, changing and/or adapting the orientation of the imaging device. Advantageously, such optimized orientation parameter may comprise an instruction how to change the position of the device from the actual orientation to an optimized orientation that is in line with a positioning guideline. Such instruction might then be shown to a user together with the signal indicative for a positioning discrepancy, for example. Alternatively, such instruction might suitably be provided to a control unit for changing a position of the device automatically upon a user providing input in response to the signal indicative for a positioning discrepancy being provided to him. In an example of the system, the system can receive real-time image data from which the intervention focus can be determined. In addition to that, the system may be capable of detecting a type of the intervention directly from analyzing the image data stream for example using a machine learning technique Alternatively or in addition, a type of procedure or intervention can be determined for example by reading an examination card and/or manual entry.

Furthermore, the intervention focus can be determined with the help of logs and reports from previous interventions or previous steps in the current intervention. For example, this may involve analyzing logging information as has been described in an article by Patil et al., "A machine learning framework for auto classification of imaging system exams in hospital setting for utilization optimization", Conference proceedings: Annual International Conference of the IEEE Engineering in Medicine and Biology Society, volume 2016, pages 2423-2426), August 2016.

Based on the detected type of intervention, a guideline can be retrieved by the system which comprises for example one or more guideline position parameters for preferred orientations of the imaging device at certain steps of the intervention. Optionally, the positioning guideline may further comprise threshold values for allowable deviations from the preferred orientations. Alternatively, a thresh By comparing the current orientation parameter of the imaging device and a guideline position parameter corresponding to the determined intervention focus, an exploitation hint and/or a statistics can be outputted by the system.

The intervention focus may refer to an intervention step and/or a sequence of, in particular successive, intervention steps. The intervention steps can be imaged by the imaging device over time. In particular, a plurality of images can be acquired over time, thereby representing an intervention step and/or a sequence of interventions steps.

For example, during a coronary stenting procedure (PCI), there may be several steps, such as: access though femoral, navigation of catheter up to the coronary tree ostium, assessment of the coronary tree (angiograms), wiring of one or several branches, navigation to stenosis and stenosis passing, stent positioning, stent delivery and many other examples of steps of the intervention within the intervention focus. Each of the interventions steps can be imaged and within each of the images the intervention focus can be determined and/or an optimized orientation parameter can be calculated. In addition, the identification unit can be configured for determining and/or receiving a type of the intervention, and/or for identifying and/or determining the intervention focus, wherein the intervention focus can be at least partially directed to a step of the intervention and/or a sequence of steps of the intervention. In addition, the compliance unit can optionally be configured for calculating an optimized orientation parameter for every step of the intervention of the received intervention focus. For example, the identification unit can be capable of determining the intervention focus, e.g.

global intervention (PCI), and the intervention step (for instance Stenting). Furthermore, the identification unit can be configured for identifying a type of the anatomical element. Furthermore, the compliance unit can be configured for calculating the optimized orientation parameter based on the type of the anatomical element within the intervention focus and/or the step of the intervention. For example, the identification unit can identify a MID RCA segment which is stented, thereby identifying the anatomical element and the step of the intervention.

According to an embodiment, the compliance unit is configured for calculating a deviation between the orientation parameter and the predefined threshold, and wherein the compliance unit is configured for calculating the optimized orientation parameter such that the deviation is minimized.

The advantage of this embodiment can be that by minimizing the deviation, the imaging quality of the image data can be improved since the orientation of the medical imaging device can enhance the acquisition of medical images.

In other words, the compliance unit can be configured for calculating, detecting and/or assessing a deviation, a delta and/or a spread between the actual orientation parameter and the guideline position parameter relative to a predefined threshold. Furthermore, the compliance unit can be configured for calculating, generating and/or outputting an optimized orientation parameter such that the deviation is minimized, lessened and/or diminished. In an example, the system calculates the optimized orientation parameter which thereby urges a treating physician to amend the orientation of the medical imaging device thereby for example increasing the image quality.

According to an embodiment, the compliance unit is configured for generating a command signal or control signal based on the optimized orientation parameter. For example, the command signal may comprise commands instructing a user to adjust the imaging device which will minimize the deviation. Alternatively or in addition, a control signal can be supplied to a suitably programmed control unit configured to automatically change the orientation of the imaging device so that the deviation will be minimized.

Preferably, such automatic change is effectuated following a user providing an input or response to a signal indicating that the deviation in the current orientation of the device with respect to the guideline position exceeds a threshold.

The advantage of this embodiment can be that with the help of the command signals, the user knows exactly how to interpret the change of orientation of the medical imaging device thereby increasing the usability of the medical imaging device and supporting the intervention.

In other words, the compliance unit is configured for generating respectively dispensing a command signal and/or a command data element based on the optimized orientation parameter and/or resulting from the optimized orientation parameter. Furthermore, the command signal can comprise and/or can have commands respectively hints instructing respectively leading a user, in particular a user of the medical imaging device, to adjust and/or change the orientation of the imaging device, which will minimize respectively reduce the deviation. In an example, the system outputs a signal for a user of the medical imaging device and/or the system which indicates a change of the orientation of the medical imaging device which can lead to a deviation reduction and therefore to an increase of the image quality of the images acquired by the medical imaging device.

According to an embodiment, the orientation parameter and/or the optimized orientation parameter is a geometrical parameter and/or an angulation parameter of the imaging device and/or of an operating table of the imaging device.

In other words, the orientation parameter indicates the position of the medical imaging device. Furthermore, the orientation parameter can be indicative for an angulation of the imaging device. Furthermore, the improved orientation parameter can indicate a change of the geometrical position and/or parameter of the medical imaging device and furthermore can be indicative for a change of the angulation and/or orientation of the imaging device. Furthermore, the improved orientation parameter can comprise a position and/or a change of the position of an operating table which can be comprised by the medical imaging device. According to an embodiment, the identification unit is configured for determining the intervention focus based on the image data. Furthermore, the identification unit is configured for identifying an intervention device, e.g. a medical intervention tool, used in the intervention and the anatomical region of the intervention based on the image data. In addition, the determination of the intervention focus is further based on the identified device and the identified anatomical region.

This embodiment can have the advantage that with the help of the identification of the device and the medical region, in particular the device in relation to the anatomical region, the determination of the intervention focus can be further improved.

In other words, the identification unit is configured for calculating respectively determining the intervention focus based on the image data and/or by evaluating the image data to determine the intervention focus. Furthermore, the identification unit is configured for identifying and/or detecting a device, in particular a surgical instrument used in the intervention, and the anatomical region respectively the region within the body which is undergoing the intervention of the intervention based on the image data and/or by evaluating the image data. In addition, the determination of the intervention focus is further based and/or incorporates the identified device and the identified anatomical region. In an example, the identification unit is configured for automatically determining the intervention focus based on the image data or a medical image and can thereby identify a device and an anatomical region within the medical image. The determination of the intervention focus can be further improved by incorporating the identified device and the identified anatomical region.

According to an embodiment, the identification unit is configured for identifying a position and/or an orientation of the device, used in the intervention and depicted in the medical image data. Furthermore, the determination of the intervention focus is further based on the position and/or orientation of the device.

This embodiment can have the advantage that by the identification of the position and/or orientation of the device, the determination of the intervention focus can be further improved.

In other words, the identification unit is configured for identifying respectively detecting a position, a position within the medical image and/or an orientation of the device respectively an orientation of the device in the body undergoing the invention, used in the intervention based on the medical image data. Furthermore, the determination of the intervention focus is further based respectively incorporates the position and/or the orientation of the device.

According to an embodiment, the identification unit is configured for identifying an anatomical element within the anatomical region pictured in the image data and/or report and log data element. Furthermore, the identification unit is configured for determining a position and/or an orientation of the anatomical element in the image data and/or the report and log data element. Furthermore, the determination of the intervention focus is further based on the position and/or the orientation of the anatomical element in the image data.

The advantage of this embodiment can be that with the help of the identification of the anatomical element, the determination of the intervention focus can be improved since the identification unit is capable of identifying a type or the sort of the anatomical element which is undergoing the invention.

In other words, the identification unit is configured for identifying respectively detecting an anatomical element, a body part and/or an organ within the anatomical region in the image data and/or a report and log data element indicative for interventions stored in a database. Furthermore, the identification unit is configured for determining and/or calculating a position, in particular a position in the medical image and/or an orientation of the anatomical element, in particular an orientation of the anatomical element within the body undergoing the intervention, in the image data and/or the report and log data element. Furthermore, the determination of the intervention focus is further based on respectively incorporates the position and/or the orientation of the anatomical element in the image data.

In an example, the identification unit is configured for identifying an anatomical element within the anatomical region. For example, the identification unit may concentrate on the bones (spine), on the diaphragm, and/or on the coronary arteries. Based on the position and orientation of these or other anatomical features in an image, the determination of the intervention focus can be further improved.

In addition or alternatively the identification unit is configured to identify an interventional device within an image. For example, the identification unit may concentrate on a guidewire tip, balloon and/or stent, analyzing the presence and dynamic behavior of such elements in a sequence of images. Based on this, the determination of the intervention focus can be further improved. As an illustrative example, balloon deployment of a wrapped stent indicates without ambiguity that stenting occurs at the balloon location.

According to an embodiment, the identification unit is configured for correlating the device with the anatomical region by a registration of a fluoroscopic image data of the intervention.

This embodiment can have the advantage, that the position of the device and the orientation of the anatomical region can be correlated and therefore the usability of the intervention can be further improved.

In other words, the identification unit is configured for correlating, interrelating and/or linking the device with the anatomical region within the fluoroscopic image data. The correlation between the device and the anatomical region can be used for the navigation of the device. Furthermore, the correlation can be used for positioning and delivery with the angiographic data in order to visualize vessels and cavities. In an example, the device is introduced in a human body, in particular in the anatomical region. In order to be able to further determine the intervention focus, the correlation of the device with the anatomical region is performed by the registration of fluoroscopy (idem).

According to an embodiment, the system further comprises a decision unit. The decision unit is configured to statistically evaluate a result of the comparison between the predefined threshold with the orientation parameter.

This embodiment can have the advantage that with the help of the decision unit, the comparison between the predefined threshold and the orientation parameter can be compared to other interventions and/or to other treating physicians such that the reliability of the intervention can be further improved.

In other words, the decision unit and/or the decision logic is configured to statistically evaluate and/or to compile statistics of a result of the comparison between the predefined threshold with the orientation parameter and/or by comparing the predefined threshold with the orientation parameter.

According to an embodiment, the decision unit is configured for dynamically adapting the intervention focus throughout an interventional procedure.

The advantage of this embodiment can be that with the help of the decision unit, a change of the intervention within one interventional procedure can be identified and the intervention focus can be adapted for example to a new subtype of intervention and/or a new anatomical element, for example an element switch for example from a liver to a stomach.

In other words, the decision unit is configured for dynamically adapting respectively event-based changing the intervention focus based on the received image data and/or the image focus throughout an interventional procedure.

According to an embodiment, the system comprises an artificial intelligence (AI) module. Furthermore, the AI module is configured for identifying a type of the intervention based on the image data.

The advantage of this embodiment can be that with the help of the AI module, the type of the intervention can be determined based on the image data respectively medical images within seconds.

In other words, the system can comprise respectively can contain an AI module, an AI logic and/or an AI interface. Furthermore, the AI module can be configured for identifying, assessing and/or calculating a type of the intervention and/or surgery respectively a medical procedure based on the image data and/or based on logging information.

According to an embodiment, the compliance unit is configured for adapting the predefined threshold based on the determined type of the intervention.

This embodiment can have the advantage that based on the determined type of intervention, the predefined threshold can be adjusted such that the usability and reliability of the intervention can be further improved.

In other words, the compliance unit is configured for adapting, fitting and/or customizing the predefined threshold respectively boundary value based on and/or in dependency of the determined type of the intervention.

A second aspect of the invention is a computer-implemented method wherein the method comprises the steps of:
  receiving image data representing an intervention;
  identifying an interventional device used in the intervention and an anatomical region of the intervention, based on the image data,
  determining an intervention focus on the basis of the identified device and the identified anatomical region,
  determining an orientation parameter indicative for an orientation of an imaging device, when generating the image data,
  receiving a guideline corresponding to a type of intervention,
  determining, based on the guideline, a guideline position parameter corresponding to the intervention focus,
  comparing the determined guideline position parameter and the received orientation parameter d,
  calculating a deviation between the guideline position parameter and the orientation parameter, and,
  generating a signal indicative of a positioning discrepancy if the calculated deviation exceeds a pre-defined threshold.

Furthermore, the received intervention focus may be indicative of (or specifies, or reflects) which intervention is depicted in the image data and reflects which anatomical region is undergoing the intervention depicted in the image data.

The advantage of this embodiment is that the positioning of an imaging device can be improved during intervention. By providing a solution for such a dynamic process, the usability of an imaging device during an intervention can be improved. Furthermore, this embodiment can comprise the advantage that with the help of the supervising of the intervention, a controlling factor can be implemented, which is further increasing the reliability of the intervention. In addition, predefined guidelines can be used in order to increase the usability of the imaging device during an intervention since the system is capable of comparing the current situation of the intervention with the predefined guidelines.

In other words, the method can comprise a receiving, downloading and/or assessing an intervention focus based on image data of an intervention acquired by an imaging device, in particular a medical imaging device. Furthermore, the method can comprise the step of determining respectively calculating an orientation parameter indicative for an orientation of the imaging device during generation of the image data, in particular during acquisition of medical images with the help of the medical imaging device. Furthermore, the method can comprise the step of comparing, matching and/or checking the determined orientation parameter and the predefined threshold. In addition, the method can comprise the step of calculating respectively determining an optimized orientation parameter, in particular an optimized orientation parameter for amending the orientation of the imaging device, in particular the orientation of a medical imaging device. Furthermore, the method can comprise the step of generating and/or outputting a signal indicative for the orientation of the imaging device based on the calculated optimized orientation parameter, in particular a signal for changing the orientation of the imaging device based on the calculated optimized orientation parameter. Furthermore, the received intervention focus specifies which intervention is performed in the image data and specifies which anatomical region is treated by the intervention in the image data.

A third aspect of the invention is a computer program which, when executed on a processor, instructs the processor to perform the method as described before and hereinafter. For example, the computer program can be stored in a memory of the system. The computer program can be run on a single computer, a plurality of computers and/or a cloud computing structure.

The fourth aspect of the invention is an imaging device, in particular a medical imaging device, which comprises a system as described before and hereinafter and/or a computer-readable medium on which a computer program as described before and hereinafter is stored. The computer-readable medium may be a storage medium, such as a USB flash drive, CD, DVD, data storage device, server, hard disk, or other medium on which a computer program as described above can be stored.

All disclosures as described here in relation to any aspect of the invention applies equally to all other aspects of the invention.

In the following, examples and embodiments of the invention are described with reference to the figures.

DETAILED DESCRIPTION OF EMBODIMENTS

Figure 1:
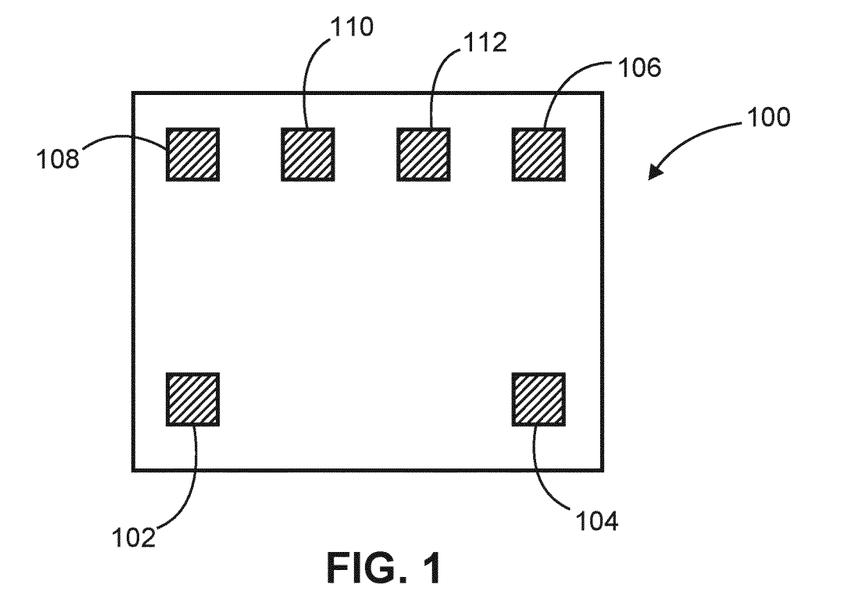
FIG. 1 shows a system for imaging processing according to an embodiment.

FIG. 1 shows a system 100 for imaging processing, wherein the system 100 comprises an identification unit 102 and a compliance unit 104. The identification unit 102 is configured for determining an intervention focus 200. The determined intervention focus 200 specifies which intervention is performed in an image data and specifies which anatomical region 202 is treated by the intervention in the image data. Furthermore, the identification unit 102 is configured for determining an orientation parameter indicative for an orientation 302 of an imaging device 300 during generation of the image data.

In addition, the compliance unit 104 is configured to receive a guideline corresponding to a type of intervention. Based on the guideline, a guideline position parameter corresponding to the intervention focus is determined, which parameter is compared with the current orientation parameter. A deviation between the guideline position parameter and the orientation parameter is calculated.

The compliance unit 104 is further configured to receive, determine or store a predefined threshold for the orientation parameter specific for the received intervention focus 200. In addition, the compliance unit 104 is configured for comparing the calculated deviation and the predefined threshold.

In certain embodiments, furthermore, the compliance unit 104 is optionally configured for calculating an optimized orientation parameter for amending the orientation 302 of the imaging device 300. Furthermore, the compliance unit 104 may be configured for generating a control signal for changing the orientation 302 of the imaging device 300 based on the calculated optimized orientation parameter.

The advantage of this embodiment is that the positioning of a imaging device 300 can be improved during intervention. By providing a solution for such a dynamic process, the usability of an imaging device 300 during an intervention can be improved. Furthermore, this embodiment can comprise the advantage that with the help of the supervising of the intervention, a controlling factor can be implemented, which is further increasing the reliability of the intervention. In addition, predefined guidelines can be used in order to increase the usability of the imaging device 300 during an intervention since the system is capable of comparing the current situation of the intervention with the predefined guidelines.

As can be seen in FIG. 1, the system 100 comprises the identification unit 102. The identification unit 102 can be configured for determining an intervention focus 200, for example by determining an intervention focus 200 based on medical image data Furthermore, the identification unit 102 is configured to determine an orientation parameter indicative for an orientation 302 of an imaging device 300.

In particular, the identification unit 102 is configured for determining the intervention focus 200 based on the image data. Furthermore, the identification unit 102 is configured for identifying a device 204 and the anatomical region 202 in the image data. Additionally, the identification unit 102 is configured for identifying a position 206 and/or the orientation 208 of the device 204 within the medical image data. Furthermore, the identification unit 102 is configured for identifying an anatomical element 210, for example a coronary artery in the medical image data. Furthermore, the identification unit 102 is configured to determine a position 212 and an orientation 214 of the anatomical element 210 in the image data and/or in a report and/or log data element.

In addition, in certain embodiments the identification unit 102 is configured for correlating the device 204 with the anatomical region 202 with the help of the registration of fluoroscopy (idem) within the medical image data.

In certain embodiment, the compliance unit 104 is configured for generating a control signal for changing the orientation 302 of the imaging device 300, in particular so as to minimize the deviation between the guideline position parameter and the actual orientation parameter. In addition, the compliance unit 104 may be configured for generating a command signal. The command signal comprises commands instructing a user 400 to adjust the position and/or the orientation of the imaging device 300 accordingly.

Furthermore, the compliance unit 104 is configured for adapting the predefined threshold based on the determined type of the intervention. Alternatively or in addition, the predefined threshold may be obtained from the guideline along with the guideline position parameter.

Furthermore, the system 100 comprises a decision unit 106 which is configured to statistically evaluate a result of the comparison between the predefined threshold with the orientation parameter. In addition, the decision unit 106 is configured for dynamically adapting the intervention focus 200 throughout an interventional procedure. In addition, the system 100 comprises an artificial (AI) module 108. The AI module 108 is configured for identifying a type of the intervention based on the image data. Furthermore, the system 100 can comprise a user interface 110 which is configured for receiving a type of intervention or an intervention focus 200. In addition, the system 100 can comprise a logging unit 112 which is configured to record the intervention and in particular data and logs of the intervention focus 200 in order to create a report and log data element.

Figure 2:
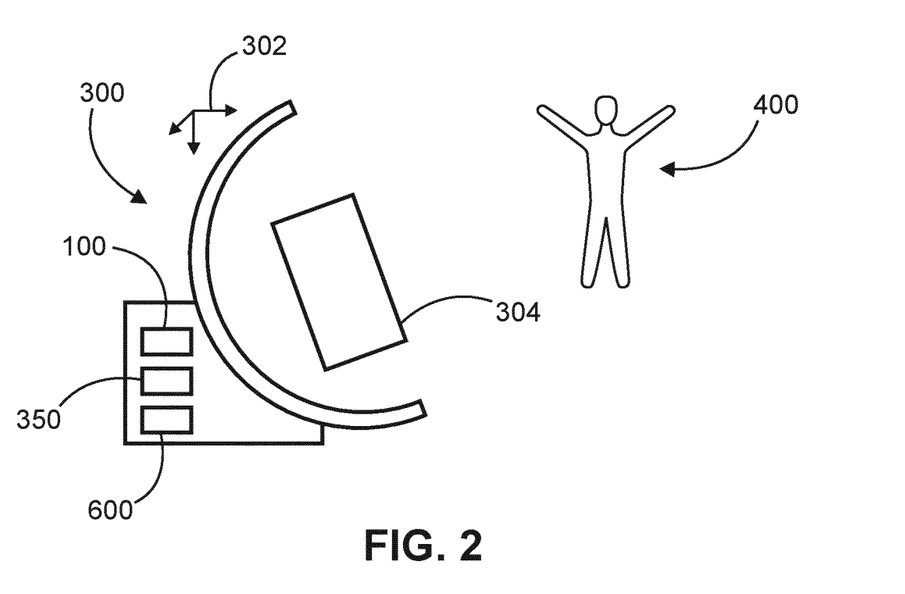
FIG. 2 shows a medical imaging device according to an embodiment.

FIG. 2 shows an imaging device 300 which comprises a system 100 as described before and hereinafter. In addition, the imaging device 300 comprises a computer-readable medium 600 on which a computer program as described before and herein later is stored. In addition, the imaging device can comprise an interface element 350 which is configured to interact with a user 400 of the imaging device 300. The interface element 350 can for example indicate a change of the orientation 302 of the imaging device 300. Furthermore, the imaging device can comprise the operating table 304, wherein the interface element 350 can output signals which indicate a change of orientation of the operating table 304.

Figure 3:
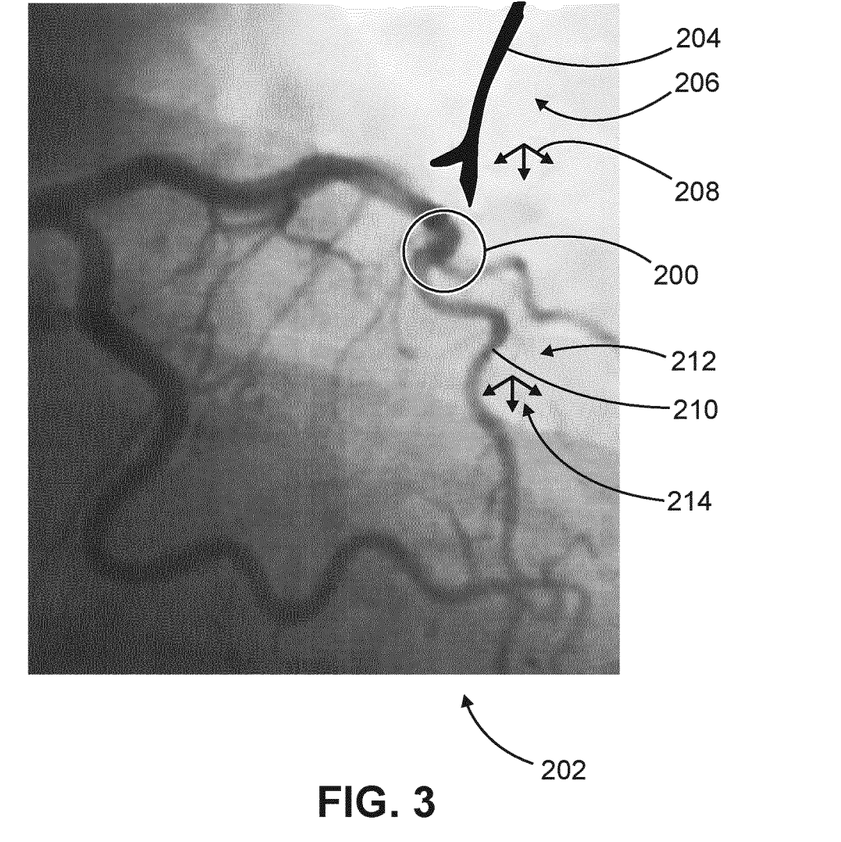
FIG. 3 shows a schematic intervention focus according to an embodiment.

FIG. 3 shows an intervention focus 200 of an anatomical region 202. Within the intervention focus 200, a device 204 can be identified. The device 204 can be located within the image data according to a position 206. Furthermore, the orientation 208 of the device can be identified within the intervention focus 200. Furthermore, within the intervention focus 200 and/or the anatomical region 202, an anatomical element 210 can be identified. Furthermore, the position 212 of the anatomical element 210 can be assessed. In addition, the orientation 214 of the anatomical element 210 can be assessed with the help of the system 100.

Figure 4:
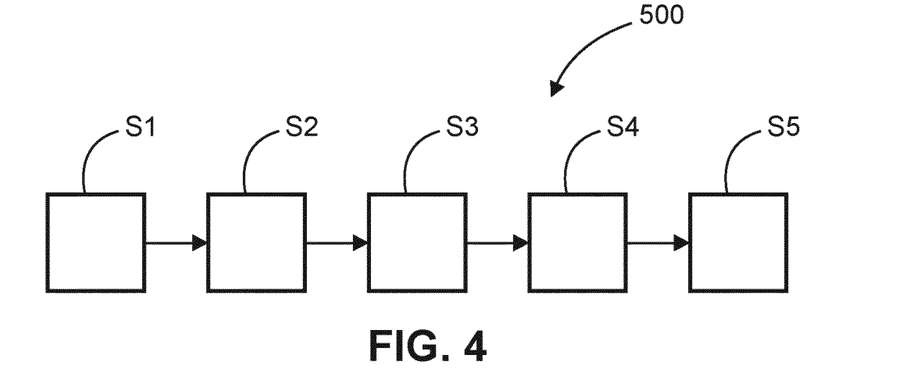
FIG. 4 shows a flow-chart diagram illustrating the method according to an embodiment.

FIG. 4 shows a flow-chart diagram illustrating the method 500. The method 500 comprises the step S1 of determining an intervention focus from image data representing an intervention and particularly on the basis of an interventional device and/or anatomical region identified in said image data. Furthermore, the method 500 comprises a step S2 of determining an orientation parameter. Furthermore, the method 500 comprises the step S3 of comparing a guideline position parameter determined from a guideline corresponding to a type of intervention to the determined orientation parameter. In addition, the method 500 comprises the step S4 of calculating a deviation between the guideline position parameter and the orientation parameter. Furthermore, the method 500 comprises a step of generating S5 a signal indicative of a positioning discrepancy.

Where an indefinite or definite article is used when referring to a singular noun, e.g. "a", "an" or "the", this includes the plurality of the noun unless something else is specifically stated. It is to be understood that the terms so used are interchangeable under appropriate circumstances and that the embodiments of the invention described here are capable of operating in other sequences than described or illustrated herein.

LIST OF REFERENCE SIGNS

100—system
102—identification unit
104—compliance unit
106—decision unit
108—AI module
110—interface
112—logging unit
200—intervention focus
202—anatomical region
204—device
206—position
208—orientation
210—anatomical element
212—position
214—orientation
300—imaging device
302—orientation
304—operating table
350—interface
400—user
500—method
600—computer-readable medium
S1—receiving an intervention focus
S2—determining an orientation parameter
S3—comparing
S4—calculating an optimized orientation parameter
S5—generating

The invention claimed is:

1. A system for image processing, the system comprising:
a processor in communication with memory, the processor configured to:
receive image data representing an intervention and identify an interventional device used in the intervention and an anatomical region of the intervention, based on the image data,
determine an intervention focus on the basis of the identified device and the identified anatomical region,
determine an orientation parameter indicative for an orientation of an imaging device generating the image data,
receive a guideline corresponding to a type of the intervention,
determine, based on the guideline, a guideline position parameter corresponding to the intervention focus and to compare the determined guideline position parameter and the determined orientation parameter and to calculate a deviation between the guideline position parameter and the orientation parameter, and
generate a signal indicative of a positioning discrepancy if the calculated deviation exceeds a pre-defined threshold.

2. The system according to claim 1, wherein the processor is further configured to calculate an optimized orientation parameter for the orientation of the imaging device such that the deviation is minimized.

3. The system according to claim 2,
wherein the processor is further configured to generate a command signal based on the optimized orientation parameter, and
wherein the command signal comprises commands instructing a user to adjust the imaging device, which will minimize the deviation.

4. The system according to claim 2,
wherein at least one of the orientation parameter and the optimized orientation parameter is at least one of a geometrical parameter and an angulation parameter of at least one of the imaging device and of an operating table of the imaging device.

5. The system according to claim 1,
wherein the processor is further configured to identify at least one of a position and an orientation of the device, used in the intervention and depicted in the image data, and wherein the processor is further configured to determine the intervention focus further based on at least one of the position and the orientation of the device.

6. The system according to claim 1, wherein the processor is further configured to:
identify an anatomical element within the anatomical region depicted in at least one of the image data and/or a report and log data element,
determine at least one of a position and an orientation of the anatomical element in at least one of the image data and the report and log data element,
wherein the processor is configured to determine the intervention focus further based on at least one of the position and the orientation of the anatomical element depicted in the image data.

7. The system according to claim 1, wherein the processor is further configured to correlate the device with the anatomical region by a registration of a fluoroscopic image data of the intervention.

8. The system according to claim 1, the processor is further configured to statistically evaluate a result of the comparison between the pre-defined threshold with the orientation parameter.

9. The system according to claim 1, wherein the processor is further configured to dynamically adapt the intervention focus throughout an interventional procedure.

10. The system according to claim 1, wherein the system comprises an artificial-intelligence (AI) module configured to identify the type of the intervention based on analyzing at least one of the image data and analyzing logging information.

11. The system according to claim 10, wherein the processor is further configured to adapt the pre-defined threshold based on the determined type of the intervention.

12. A computer-implemented method, comprising:
receiving image data representing an intervention;
identifying an interventional device used in the intervention and an anatomical region of the intervention, based on the image data,
determining an intervention focus on the basis of the identified device and the identified anatomical region,
determining an actual orientation parameter indicative for an orientation of an imaging device, when generating the image data,
receiving a guideline corresponding to a type of intervention,
determining, based on the guideline, a guideline position parameter corresponding to the intervention focus,
comparing the determined guideline position parameter and the determined orientation parameter,
calculating a deviation between the guideline position parameter and the orientation parameter, and
generating a signal indicative of a positioning discrepancy if the calculated deviation exceeds a pre-defined threshold.

13. A non-transitory computer-readable storage medium having stored a computer program comprising instructions, which, when executed by a processor, cause the processor to:
receive image data representing an intervention;
identify an interventional device used in the intervention and an anatomical region of the intervention, based on the image data,
determine an intervention focus on the basis of the identified device and the identified anatomical region,
determine an actual orientation parameter indicative for an orientation of an imaging device, when generating the image data,
receive a guideline corresponding to a type of intervention,
determine, based on the guideline, a guideline position parameter corresponding to the intervention focus,
compare the determined guideline position parameter and the determined orientation parameter,
calculate a deviation between the guideline position parameter and the orientation parameter, and
generate a signal indicative of a positioning discrepancy if the calculated deviation exceeds a pre-defined threshold.

* * * * *